United States Patent
Watanabe et al.

(10) Patent No.: US 7,267,750 B2
(45) Date of Patent: Sep. 11, 2007

(54) BIOSENSOR

(75) Inventors: Motokazu Watanabe, Toyonaka (JP); Tomohiro Yamamoto, Hirakata (JP); Miwa Hasegawa, Hyogo (JP); Shin Ikeda, Katano (JP); Shiro Nankai, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 821 days.

(21) Appl. No.: 10/466,561

(22) PCT Filed: Jan. 10, 2002

(86) PCT No.: PCT/JP02/00108

§ 371 (c)(1),
(2), (4) Date: Jul. 17, 2003

(87) PCT Pub. No.: WO02/057767

PCT Pub. Date: Jul. 25, 2002

(65) Prior Publication Data

US 2004/0069628 A1    Apr. 15, 2004

(30) Foreign Application Priority Data

Jan. 17, 2001    (JP) ............... 2001-008473

(51) Int. Cl.
  *G01N 27/327*    (2006.01)
(52) U.S. Cl. ............... 204/403.04; 204/403.14
(58) Field of Classification Search ........ 204/403.01–403.15; 205/777.5, 778

See application file for complete search history.

(56) References Cited

U.S. PATENT DOCUMENTS

| 5,658,443 A | 8/1997 | Yamamoto et al. |
| 6,033,866 A | 3/2000 | Guo et al. |
| 6,214,612 B1 | 4/2001 | Yamamoto et al. |

FOREIGN PATENT DOCUMENTS

| CN | 1219676 A | 6/1999 |
| EP | 1118675 A2 * | 7/2001 |
| EP | 1 124 131 A2 | 8/2001 |
| JP | 63-317096 | 12/1988 |

(Continued)

OTHER PUBLICATIONS

The JPO English language machine translation of Tomohiro et al. (JP 09-297121 A).*
Wikipedia "Lecithin" entry downloaded Dec. 7, 2006.*
JPO English language translation of JP 10-197473A.*
By the JPO English language translation of JP 11-304748 A.*

(Continued)

*Primary Examiner*—Alex Noguerola
(74) *Attorney, Agent, or Firm*—McDermott Will & Emery LLP

(57) ABSTRACT

A biosensor comprising: an electrically insulating base plate; an electrode system comprising a working electrode and a counter electrode formed on the base plate; a cover member which is joined to the base plate to form a sample solution supply pathway for supplying a sample solution to the electrode system between the cover member and the base plate; and a reagent system comprising at least an oxidoreductase and an electron mediator disposed in the sample solution supply pathway, wherein the electron mediator is provided on the base plate and the oxidoreductase is provided on the cover member such that the electron mediator and the oxidoreductase are not in contact with each other.

13 Claims, 4 Drawing Sheets

FOREIGN PATENT DOCUMENTS

| | | |
|---|---|---|
| JP | 2-62952 | 3/1990 |
| JP | 2-102448 | 4/1990 |
| JP | 2-157646 | 6/1990 |
| JP | 3-54447 | 3/1991 |
| JP | 7-83872 | 3/1995 |
| JP | 7-110303 | 4/1995 |
| JP | 08-304328 A | 11/1996 |
| JP | 9-288079 | 11/1997 |
| JP | 9-297121 | 11/1997 |
| JP | 10-197473 | 7/1998 |
| JP | 10-232219 | 9/1998 |
| JP | 11-2618 | 1/1999 |
| JP | 11-101771 | 4/1999 |
| JP | 11-304748 | 11/1999 |
| JP | 2000-39416 | 2/2000 |
| JP | 2001-183330 | 7/2001 |
| JP | 2001-201479 | 7/2001 |
| JP | 2001-343348 | 12/2001 |

OTHER PUBLICATIONS

JPO English language translation of JP 07-83872 A.*
JPO English language translation of JP 2000-39416 A.*
The JPO English language machine translation of Tomohiro et al. (JP 09-297121 A), Nov. 18, 1997.*
JPO English language translation of JP 10-197473A, Jul. 31, 1998.*
By the JPO English language translation of JP 11-304748 A, Nov. 5, 1999.*
European Search Report for Corresponding Application No. 02 73 2186 mailed Dec. 19, 2006.

* cited by examiner

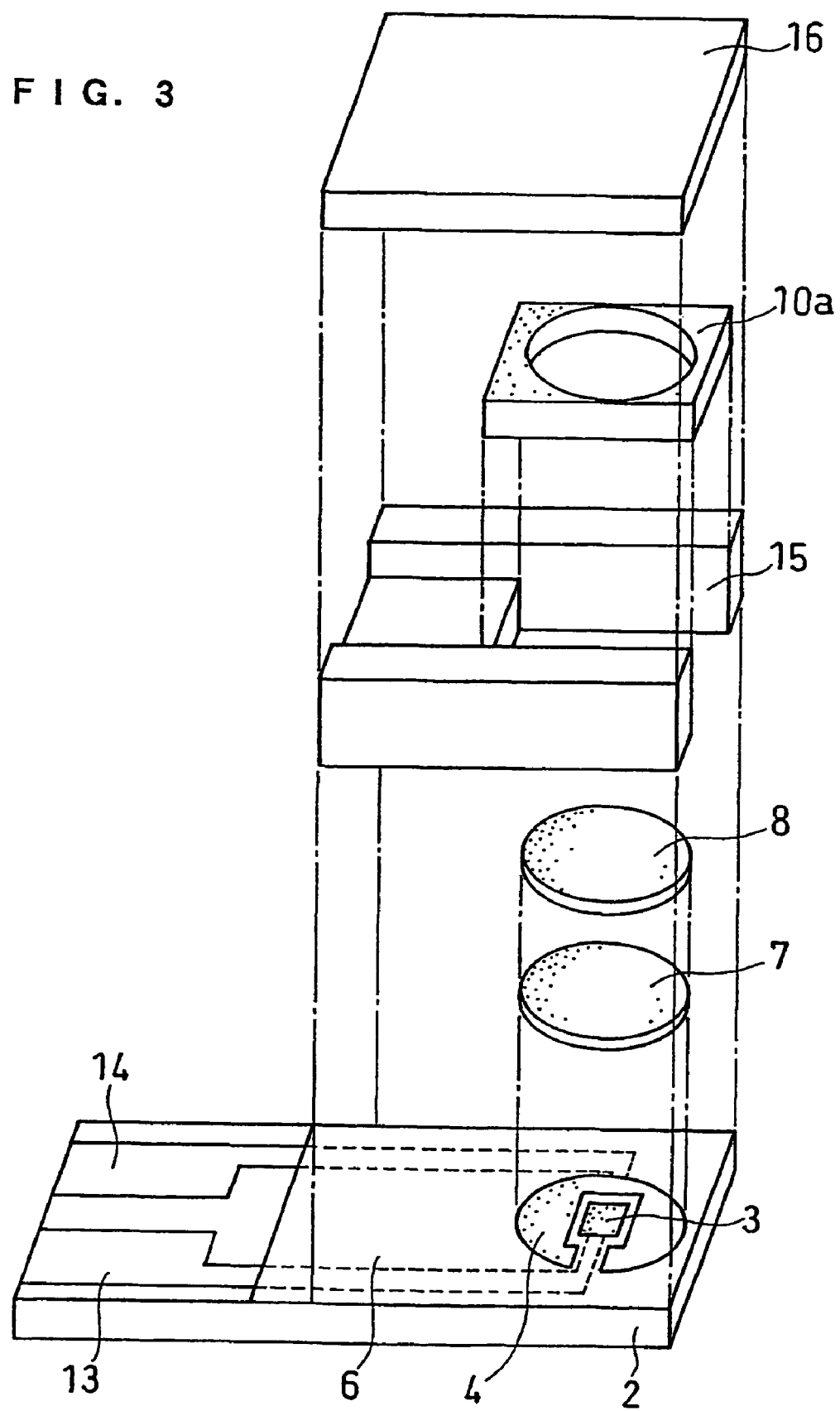
F I G. 3

BIOSENSOR

This application is a 371 of PCT/JP02/00108, filed Jan. 10, 2002, and also claims priority from Japanese application JP 2001-008473, filed Jan. 27, 2001.

TECHNICAL FIELD

The present invention relates to a biosensor for quantifying a substrate contained in a sample, such as blood, plasma and serum.

BACKGROUND ART

Various biosensors have conventionally been proposed to quantify a specific component of a sample such as blood, and the following sensor is known as one example (Japanese Laid-Open Patent Publication No. Sho 63-317096).

This biosensor is produced by forming an electrode system comprising a working electrode, a counter electrode and a reference electrode on an insulating base plate by a method such as screen printing and forming a reaction layer comprising an oxidoreductase and an electron mediator on the electrode system.

When a sample containing a substrate is dropped on the reaction layer of the biosensor thus produced, dissolution of the reaction layer takes place to cause a reaction between the oxidoreductase and the substrate, which is accompanied by reduction of the electron mediator. After the lapse of a certain period of time, the reduced electron mediator is electrochemically oxidized by the electrode system, and based on the oxidation current value obtained, the substrate in the sample solution is quantified.

In the biosensor having the above-described constitution, the oxidoreductase and the electron mediator are usually mixed with each other on the electrode system. This is aimed at saving the trouble of mixing or stirring the sample and causing the reaction between the oxidoreductase and the electron mediator to proceed effectively such that quick quantification of the substrate becomes possible.

However, the biosensor in which the oxidoreductase and the electron mediator are mixed or in contact with each other has such a problem that the response value to a sample solution having a substrate concentration of 0 mg/dl (hereinafter referred to as blank value) is not 0 but higher than 0. Further, another problem is that in comparison with the response value immediately after the production of the biosensor (hereinafter referred to as initial stage), the blank value and the response value to a sample solution having the same substrate concentration increase as the storage period becomes longer. The response value is changed by storage becomes a problem in that the reliability is low.

In view of the above problems, an object of the present invention is to provide a biosensor of which blank value is low, of which response value, particularly blank value, is hardly changed by storage, and of which structure is simple.

Another object of the present invention is to provide a biosensor suited for quantification of cholesterol in particular.

DISCLOSURE OF INVENTION

The present invention provides a biosensor comprising: an electrically insulating base plate; an electrode system comprising a working electrode and a counter electrode formed on the base plate; a cover member which is joined to the base plate to form a sample solution supply pathway for supplying a sample solution to the electrode system between the cover member and the base plate; and a reagent system comprising at least an oxidoreductase and an electron mediator disposed in the sample solution supply pathway, wherein the electron mediator is provided on the base plate and the oxidoreductase is provided on the cover member such that the electron mediator and the oxidoreductase are not in contact with each other.

It is preferable that the oxidoreductase be positioned, when projected onto the base plate, so as not to overlap with the position of the electron mediator.

The present invention also provides a measuring system comprising: the above-described biosensor; a voltage application means for applying a voltage between the working electrode and the counter electrode; and a signal detection means for detecting an electric signal between the working electrode and the counter electrode upon application of the voltage.

It is preferable that the measuring system further comprise a display means for displaying the signal detected by the signal detection means.

BRIEF DESCRIPTION OF DRAWINGS

FIG. 3 is an exploded perspective view of a biosensor in another example of the present invention.

BEST MODE FOR CARRYING OUT THE INVENTION

Figure 1:
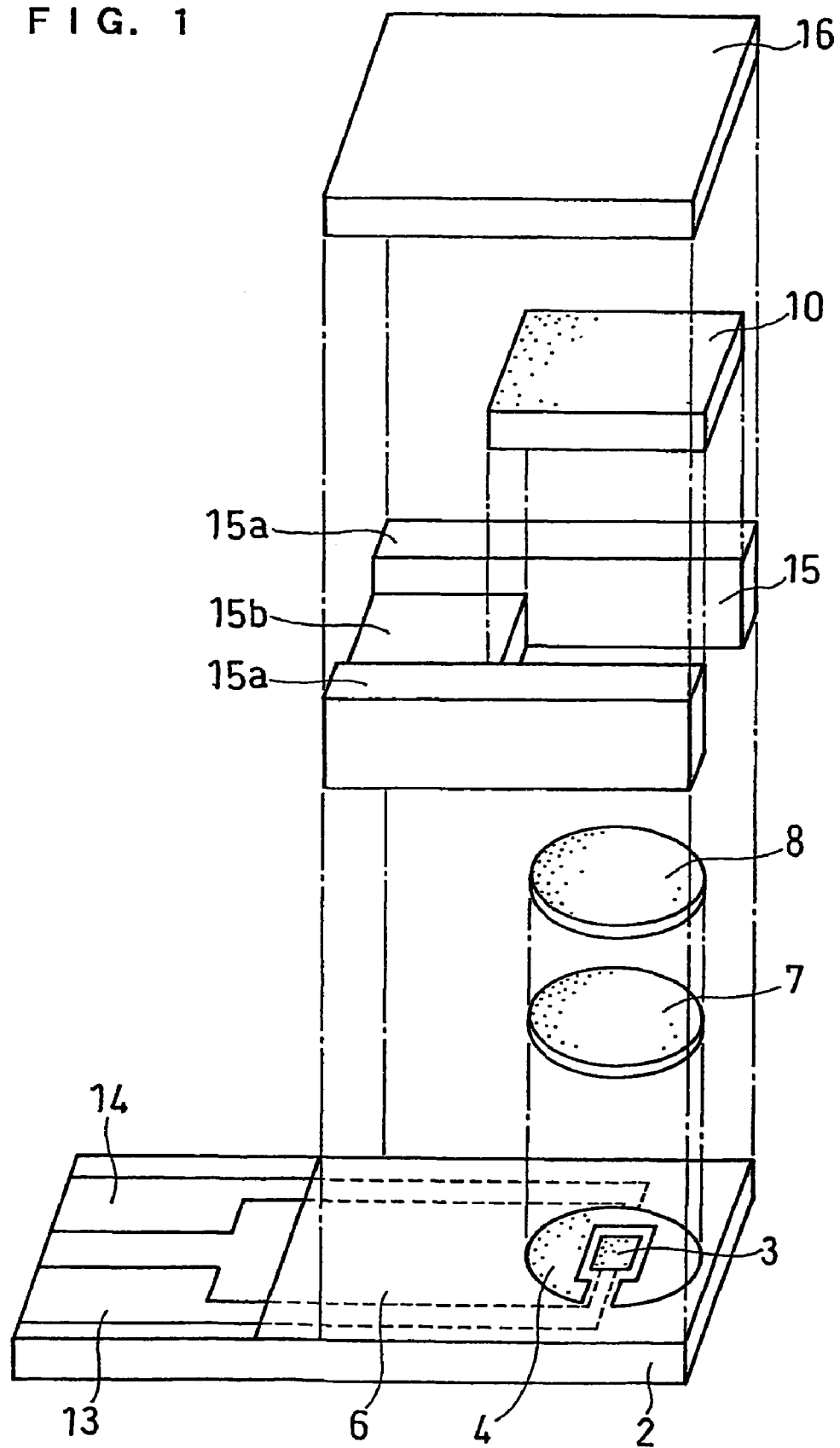
FIG. 1 is an exploded perspective view of a biosensor in one example of the present invention.

The present invention relates to a biosensor comprising: an electrically insulating base plate; an electrode system comprising a working electrode and a counter electrode formed on the base plate; a cover member which is joined to the base plate to form a sample solution supply pathway for supplying a sample solution to the electrode system between the cover member and the base plate; and a reagent system comprising at least an oxidoreductase and an electron mediator disposed in the sample solution supply pathway, wherein the electron mediator is provided on the base plate and the oxidoreductase is provided on the cover member such that the electron mediator and the oxidoreductase are not in contact with each other.

According to the present invention, the electron mediator and the oxidoreductase are prevented from coming in contact with each other in a simple structure. Thus, after the production of the biosensor, the oxidoreductase and the electron mediator do not react with each other in the biosensor, so that the blank value can be kept low and the change in the response value due to storage can be suppressed.

In a preferable mode of the present invention, the oxidoreductase is positioned, when projected onto the base plate, so as not to overlap with the position of the electron mediator.

This can reduce the volume of the sample solution supply pathway while separating the oxidoreductase from the electron mediator.

In another preferable mode of the present invention, the reagent system further comprises a surfactant provided on the cover member. In this case, it is preferable that the surfactant be mixed with the oxidoreductase.

A preferable biosensor in accordance with the present invention is designed for quantifying serum cholesterol level as a diagnostic index, and the reagent system comprises: at least one of cholesterol oxidase and cholesterol dehydrogenase; cholesterol esterase which is an enzyme catalyzing the conversion of cholesterol ester into cholesterol; and a surfactant.

Cholesterol in blood or serum is contained in lipoprotein having a micelle structure. Inclusion of an appropriate surfactant in the reagent system improves the reactivity of at least one of cholesterol oxidase and cholesterol dehydrogenase or cholesterol esterase to the cholesterol contained in lipoprotein.

The surfactant used for the above purpose may be either an ionic surfactant or a non-ionic surfactant. Such examples include polyoxyethylene-octyl phenyl ether, cholic acid or its salts, deoxycholic acid or its salts, salts of fatty acid, salts of alkylsulfate ester, salts of polyoxyethylene alkyl ether sulfate ester, alkyl benzene sulfonates, alkyl naphthalene sulfonates, alkyl sulfosuccinates, alkyl diphenyl ether disulfonates, alkyl phosphates, naphthalenesulfonic acid formalin condensation products, polycarboxylic acid type polymer surfactants, polyoxyethylene alkyl ethers, polyoxyalkylene alkyl ethers, polyoxyethylene derivatives, sorbitan fatty acid esters, polyoxyethylene sorbitan fatty acid esters, polyoxyethylene sorbitol fatty acid esters, glycerin fatty acid esters, polyoxyethylene fatty acid esters, polyoxyethylene alkyl amines, alkyl alkanol amides, alkyl amine salts, quaternary ammonium salts, alkyl betaines, and amine oxides. Among them, polyoxyethylene-octyl phenyl ether is particularly preferable.

Since the solubilizing action of the surfactant on lipoprotein varies depending on the type of the surfactant, two or more of the above-listed surfactants may be used at one time.

In another preferable mode of the present invention, at least one of the electron mediator and the oxidoreductase is formed by freeze-drying its aqueous solution.

The layer of the electron mediator and/or the oxidoreductase formed by freeze-drying has an improved dissolution, so that the time required for the whole measurement can be shortened. Since the reaction by the oxidoreductase is the first step for obtaining a response value, it is particularly preferable to form the layer of the oxidoreductase by freeze-drying, because the oxidoreductase can be promptly dissolved upon supplying a sample solution.

In still another preferable mode of the present invention, at least one of the electron mediator and the oxidoreductase is carried by a carrier.

As the carrier, any carrier capable of carrying a reagent or reagents inside or on the surface of the carrier may be used, and such examples include filter paper, glass filter, cellulose fiber, paper and cork. When filter paper is used, the reagent(s) are primarily carried inside the filter paper, and when paper is used, the reagent(s) are carried on the surface of the paper; therefore, there is a difference between them. Among these carriers, glass filter and cellulose fiber are preferable because there is less non-specific adsorption of the oxidoreductase to these carriers.

With respect to the electron mediator which can be used in the biosensor of the present invention, there is no particular limitation, but potassium ferricyanide, p-benzoquinone, derivatives of p-benzoquinone, phenazine methosulfate, methylene blue, ferrocene and derivatives of ferrocene may be used. Among them, potassium ferricyanide is preferable because it is stable in the presence of oxygen.

As the oxidoreductase, for example, glucose oxidase, glucose dehydrogenase, cholesterol oxidase, cholesterol dehydrogenase or the like is selected, as appropriate, depending on the substrate to be measured.

As the insulating base plate and the cover member, any electrically insulating material having rigidity may be used. Such examples include thermoplastic resins, such as polyethylene, polyethylene terephthalate, polystyrene, poly vinyl chloride, polyamide and saturated polyester, or thermosetting resins, such as urea resin, melamine resin, phenol resin, epoxy resin and unsaturated polyester resin.

A preferable biosensor of the present invention has an electron mediator layer which is formed over the electrode system on the base plate. In order to prevent the direct contact between the electron mediator and the electrode system and securely carry the electron mediator layer, it is preferable to form a hydrophilic polymer layer on the electrode system and form the electron mediator layer on the hydrophilic polymer layer.

Also, when the electrode system is constituted of a silver paste base and a carbon paste on the base, a sample solution permeates the silver layer of the electrode base by the action of the surfactant of the reagent system dissolved in the sample. Thus, when a potential is applied onto the electrodes for measuring the response current of the sensor, the silver layer may affect the electrochemical reaction, resulting in an increase in the response current value. When the electrode system is coated with the hydrophilic polymer layer, the permeation of the surfactant into the silver layer can be lessened.

The hydrophilic polymer constituting the hydrophilic polymer layer may be any material of which aqueous solution has viscosity, and such examples include cellulose such as carboxymethyl cellulose, hydroxyethyl cellulose, hydroxypropyl cellulose, methyl cellulose, ethyl cellulose, ethylhydroxyethyl cellulose and carboxyethyl cellulose, polyvinyl pyrrolidone, polyvinyl alcohol, polyamino acid such as polylysine, polystyrene sulfonate, gelatin and its derivatives, a polymer of acrylic acid and its salts, a polymer of methacrylic acid and its salts, starch and its derivatives, a polymer of maleic anhydride and its salts, agarose gel and its derivatives.

The material of the working electrode and the counter electrode may be any conductive material, and such examples include carbon, gold, palladium and platinum.

The electrode system comprising the working electrode and the counter electrode formed on the insulating base plate may further comprise a reference electrode.

As the sample to be measured by the biosensor of the present invention, a body fluid may be cited. The body fluid may be either one of blood, plasma, lymph fluid, interstitial fluid and sweat. The substrate to be measured is cholesterol, glucose, or the like contained in the body fluid.

In the following, the structure of the biosensor of the present invention will be described with reference to drawings. The structural drawings are used to facilitate the understanding, and the relative size and positional relationship of the respective elements are not necessarily accurate.

EMBODIMENT 1

Figure 2:
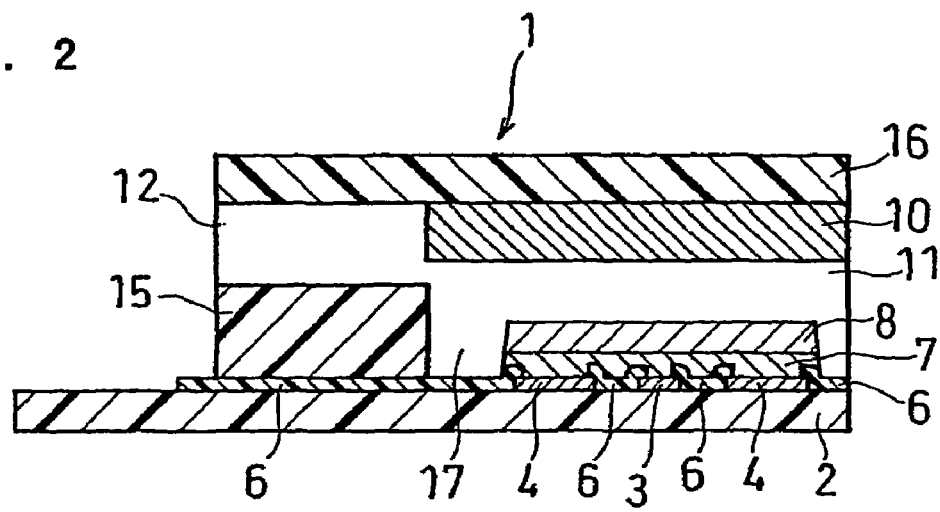
FIG. 2 is a sectional view of the biosensor.

FIG. 1 is an exploded perspective view of a biosensor of this example, and FIG. 2 is a sectional view of the biosensor.

A silver paste is printed by screen printing on an insulating base plate 2 and is dried by heating to form a working electrode lead 13 and a counter electrode lead 14 and a base of the electrode system that will be described below. Subsequently, a conductive carbon paste is printed by screen printing and dried by heating to form an electrode system consisting of a working electrode 3 and a counter electrode 4. Further, an insulating paste is printed by screen printing so as to partially cover the electrode system and is dried by heating to form an insulating layer 6. An aqueous solution of carboxymethyl cellulose (hereinafter referred to as CMC), which is a hydrophilic polymer, is dropped over the electrode system consisting of the working electrode 3 and the counter electrode 4, and is then dried by heating to form a CMC layer 7. Thereafter, an aqueous solution of potassium ferricyanide, which is an electron mediator, is dropped over the CMC layer 7 and is dried by heating, to form an electron mediator layer 8. In these figures, the CMC layer 7 and the electron mediator layer 8 are illustrated as being independent of each other, but in fact, they may be partially mixed with each other.

Next, a cover member is fabricated by joining a top cover 16 and a mid cover 15 together. The mid cover 15 is composed of two columnar members 15a and a short member 15b connecting them on the rear side. The cover member has a depression surrounded by the members 15a and 15b under the top cover 16. The cove member is turned upside down, and an enzyme layer 10 is formed by dropping a mixed aqueous solution containing cholesterol esterase, cholesterol oxidase and/or cholesterol dehydrogenase, serving as oxidoreductase, and a surfactant in the above-mentioned depression and freeze-drying it. The enzyme layer 10 is formed in such a manner as to be accommodated in a sample solution supply pathway 17 formed by laminating the top cover 16, the mid cover 15 and the insulating base plate 2. Lastly, the insulating base plate 2 and the cover member are laminated in the positional relationship as shown by the dash-dotted lines in FIG. 1, to produce a biosensor 1.

In the biosensor 1, the sample solution supply pathway 17, through which a sample solution is supplied to the electrode system, is formed by the insulating base plate 2, the mid cover 15 and the top cover 16 between the insulating base plate 2 and the top cover 16. A sample such as blood is supplied to the biosensor 1 from a sample supply inlet 11. An air vent 12 allows air to escape upon supply of the sample, serving to facilitate the supply of the sample.

In the sensor having the above-described structure, the sample solution supply pathway 17 is preferably 0.4 to 4 mm in width, 0.05 to 0.5 mm in height and 2 to 10 mm in length. For the sensor of such size, the amount of a sample required is as small as 0.04 to 20 µl. The sample solution supply pathway 17 is more preferably 0.5 to 2 mm in width, 0.05 to 0.2 mm in height and 3 to 5 mm in length, in which case the amount of a sample becomes 0.075 to 2.0 µl.

EMBODIMENT 2

Figure 4:
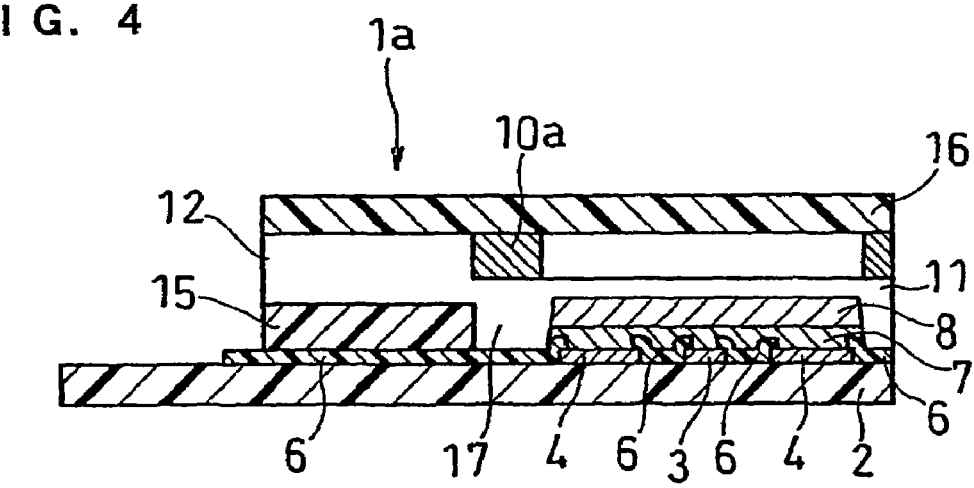
FIG. 4 is a sectional view of the biosensor.

FIG. 3 is an exploded perspective view of a biosensor of this example, and FIG. 4 is a sectional view of the biosensor.

The biosensor of this embodiment is different from that of Embodiment 1 in the formation method of the enzyme layer and the position of the formed enzyme layer. An enzyme layer 10a of this embodiment is formed by screen printing a mixed aqueous solution containing an oxidoreductase, cholesterol esterase and a surfactant on the undersurface of a top cover 16 and drying it. The position of the enzyme layer 10a is set such that when projected onto a base plate 2, the enzyme layer 10a surrounds an electron mediator layer 8 without overlapping with the layer 8.

In the biosensor of this embodiment, the enzyme layer 10a of the cover member is set such that when projected onto the base plate 2, it surrounds the electron mediator layer 8 without overlapping with the layer 8; therefore, it is possible to reduce the thickness of the sample solution supply pathway, and therefore, the volume of the sample solution supply pathway, while maintaining the separation of the oxidoreductase from the electron mediator. Accordingly, the amount of a sample necessary for the measurement can be reduced.

Further, since the oxidoreductase and the electron mediator can be carried in closer vicinity, the oxidoreductase and the electron mediator are promptly mixed with each other upon supply of the sample, so that shortening the reaction time is possible.

EMBODIMENT 3

Figure 5:
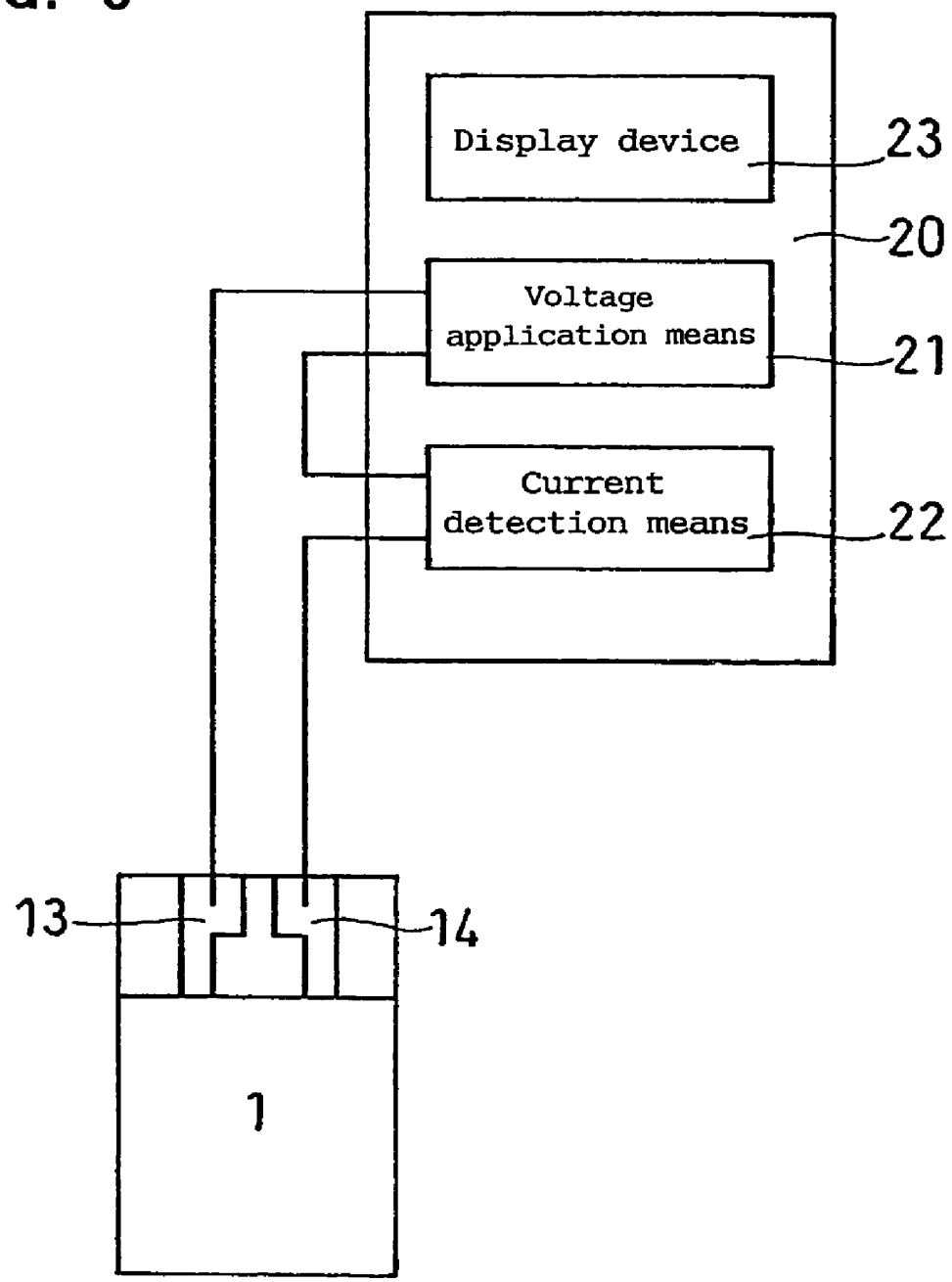
FIG. 5 is a block diagram showing the circuit structure of a measuring system in one example of the present invention.

FIG. 5 is a block diagram showing an example of the structure of a measuring system using the above-described biosensor. A voltage application means 21 applies a voltage between the working electrode 3 and the counter electrode 4 from the leads 13 and 14 of the sensor 1. A current detection means 22 placed between the voltage application means 21 and the lead 14 detects the current flowing between the working electrode 3 and the counter electrode 4. A display means 23 connected to the current detection means 22 displays the current value detected by the current detection means 22 or the value obtained by converting the current into voltage.

In the following, the present invention will be more specifically described by way of examples. As one example of the biosensor, a cholesterol sensor will be described, but the following examples are not to be construed as limiting in any way the present invention.

EXAMPLE 1

In Embodiment 1, a 0.5 wt % aqueous solution of CMC was dropped in an amount of 4 µl over the electrode system and was dried at 50° C. for 15 minutes to form the CMC layer 7. A 75 mM aqueous solution of potassium ferricyanide was dropped in an amount of 4 µl over the CMC layer 7 and was dried at 50° C. for 15 minutes to form the electron mediator layer 8. Meanwhile, a mixed aqueous solution containing 400 unit(U)/ml cholesterol oxidase, 900 U/ml cholesterol esterase, and 1.6 wt % Triton-X100 (polyoxyethylene-octyl phenyl ether, a surfactant) was dropped in an amount of 0.5 µl at a predetermined position of the cover member and was freeze-dried to form the enzyme layer 10. The sample solution supply pathway 17 is 2 mm in width, 0.1 mm in height and about 5.0 mm in length, and the area of the working electrode 3 is about 1.0 mm$^2$.

COMPARATIVE EXAMPLE 1

A biosensor of Comparative Example 1 was produced in the same manner as in Example 1 except that cholesterol esterase and cholesterol oxidase were mixed into the electron mediator layer.

Next, using the biosensors of Example 1 and Comparative Example 1, cholesterol concentrations were measured on a cholesterol-free PBS buffer solution (cholesterol concentration is 0 mg/dl and PBS designates phosphate buffered saline) and human serum having a cholesterol concentration of 105 mg/dl. The sample solution was supplied to the sample solution supply pathway 17 by bringing it into contact with the sample supply inlet 11; 3 minutes after that, a voltage of 500 mV was applied to the working electrode 3 with respect to the counter electrode 4, and 5 seconds after that, the value of the current (response value) flowing between the working electrode 3 and the counter electrode 4 was measured.

Table 1 shows changes in response value to the PBS buffer solution having a cholesterol concentration of 0 mg/dl, and Table 2 shows changes in response value to the human serum having a cholesterol concentration of 105 mg/dl. On each of the sample solutions, a comparison was made between the response value at the initial stage of the biosensor and the response value after a 4-week storage of the biosensor at 30° C.

TABLE 1

|  | Initial stage | After storage |
|---|---|---|
| Example 1 | 0.19 μA | 0.22 μA |
| Comparative Example 1 | 0.56 μA | 0.89 μA |

TABLE 2

|  | Initial stage | After storage |
|---|---|---|
| Example 1 | 1.53 μA | 1.58 μA |
| Comparative Example 1 | 2.12 μA | 2.64 μA |

As is clear from Table 1, at the initial state, the response value of the biosensor of Example 1 to the cholesterol concentration of 0 mg/dl was 0.19 μA, which was 0.37 μA lower than that of the biosensor of the comparative example. Thus, the biosensor of Example 1 produced the effect of lowering the response value to the cholesterol concentration of 0 mg/dl, i.e., the blank value.

As is also clear from Table 1, the response value of the comparative example to the cholesterol concentration of 0 mg/dl increased from 0.56 μA to 0.89 μA by 0.33 μA due to the 4-week storage at 30° C. On the other hand, the response value of Example 1 to the cholesterol concentration of 0 mg/dl increased from 0.19 μA to 0.22 μA under the same storage conditions, which was a slight increase of 0.03 μA, and hence the increase in blank value due to the storage was suppressed.

Further, as is clear from Table 2, the response value of the comparative example to the cholesterol concentration of 105 mg/dl increased from 2.12 μA to 2.64 μA by 0.52 μA due to the 4-week storage at 30° C. On the other hand, the response value of Example 1 to the cholesterol concentration of 105 mg/dl increased from 1.53 μA to 1.58 μA under the same storage conditions, which was a slight increase of 0.05 μA, and hence the increase in blank value due to the storage was suppressed.

EXAMPLE 2

In Embodiment 2, a mixed aqueous solution containing cholesterol oxidase, cholesterol esterase and Triton-X100 was used as the ink for printing the enzyme layer 10a. The obtained enzyme layer 10a contains 1.0 U cholesterol oxidase, 2.25 U cholesterol esterase and 8.0 μg Triton-X100. The enzyme layer 10a is about 0.7 mm in thickness, and the diameter of the middle hole is slightly greater than the outer shape of the counter electrode 4 (a circle 3.0 mm in diameter). The CMC layer 7 and the electron mediator layer 8 were formed in the same manner as in Example 1, and their outer shapes are almost the same as the outer shape of the counter electrode 4.

Using this biosensor, the cholesterol concentrations of the sample solutions were measured in the same procedure as in Example 1, and the results obtained were similar to those of Example 1.

In Examples 1 and 2, the CMC layer 7 and the electron mediator 8 had a round shape, but they may be square, rectangular or oval. In either case, the enzyme layer 10 or 10a may be of any shape unless the oxidoreductase comes in contact with the electron mediator.

Also, potassium ferricyanide was used as the electron mediator, but either one of p-benzoquinone and its derivatives, phenazine methosulfate, methylene blue, and ferrocene and its derivatives may also be used.

An explanation was given of the reagent system containing cholesterol esterase, cholesterol oxidase and the surfactant to measure the total cholesterol level of blood or the like, but glucose oxidase, glucose dehydrogenase or the like may be used as the oxidoreductase in a system measuring the amount of glucose.

In the foregoing examples, the layer containing the electron mediator was formed by dropping the aqueous solution of the electron mediator onto the intended position of the layer and drying it by heating, but it may be formed by dropping an aqueous solution containing the electron mediator onto the predetermined position and freeze-drying it. Also, the layer containing the electron mediator may be formed by a method of screen printing an aqueous solution containing the electron mediator or by a method of impregnating a carrier disposed in the sample solution supply pathway with an aqueous solution containing the electron mediator and heat-drying it at 30 to 70° C. or freeze-drying it.

The layer containing the oxidoreductase was formed by the method of dropping the aqueous solution of the oxidoreductase on the predetermined position and freeze-drying it or by the method of screen printing the aqueous solution containing the oxidoreductase, but it may also be formed by other methods. For example, it may be formed by a method of dropping an aqueous solution containing the oxidoreductase onto the predetermined position and heat-drying it at 30 to 70° C. or by a method of dropping an aqueous solution containing the oxidoreductase onto a carrier disposed in the sample solution supply pathway, impregnating the carrier with the aqueous solution, and heat-drying it at 30 to 70° C. or freeze-drying it.

INDUSTRIAL APPLICABILITY

As described above, the present invention can provide a biosensor of which blank value is low, of which response value, particularly blank value, is hardly changed by storage, and of which structure is simple. Further, by employing a structure that prevents the contact between an oxidoreductase and an electron mediator, the thickness of a sample supply solution supply pathway can be reduced, so that the necessary amount of a sample such as blood can be decreased. Further, since the oxidoreductase and the electron mediator can be carried in closer vicinity, the oxidoreductase and the electron mediator are promptly mixed with each other upon supply of the sample, so that shortening the reaction time is possible.

The invention claimed is:

1. A biosensor comprising: an electrically insulating base plate; an electrode system comprising a working electrode and a counter electrode formed on said base plate; a cover member which is joined to said base plate to form a sample solution supply pathway for supplying a sample solution to said electrode system between the cover member and the base plate; and a reagent system comprising at least cholesterol oxidase, cholesterol esterase, a surfactant and an electron mediator disposed in said sample solution supply pathway, wherein said electron mediator is provided on said base plate, and said cholesterol oxidase and said surfactant is provided on said cover member such that they are not in contact with said electron mediator.

2. The biosensor in accordance with claim 1, wherein said cholesterol oxidase is positioned, when projected onto said base plate, so as not to overlap with the position of said electron mediator.

3. The biosensor in accordance with claim 1, wherein said surfactant is mixed with said cholesterol oxidase.

4. The biosensor in accordance with claim 1, wherein at least one of the electron mediator and the cholesterol oxidase is produced by freeze-drying its aqueous solution.

5. The biosensor in accordance with claim 1, wherein at least one of the electron mediator and the cholesterol oxidase is carried by a carrier.

6. The biosensor in accordance with claim 5, wherein said carrier is selected from the group consisting of filter paper, glass filter, cellulose fiber, paper and cork.

7. The biosensor in accordance with claim 1, wherein said cholesterol esterase is provided on said cover member.

8. The biosensor in accordance with claim 7, wherein said electron mediator is provided over said electrode system with a hydrophilic polymer layer interposed therebetween.

9. The biosensor in accordance with claim 7, wherein said electron mediator is selected from the group consisting of potassium ferricyanide, p-benzoquinone, derivatives of p-benzoquinone, phenazine methosulfate, methylene blue, ferrocene and derivatives of ferrocene.

10. The biosensor in accordance with claim 1, which is designed to measure a body fluid.

11. The biosensor in accordance with claim 10, wherein said body fluid is blood, plasma, lymph or interstitial fluid.

12. A measuring system comprising: the biosensor as recited in claim 1; a voltage application means for applying a voltage between said working electrode and said counter electrode; and a signal detection means for detecting an electric signal between the working electrode and the counter electrode upon application of the voltage.

13. The measuring system in accordance with claim 12, further comprising a display means for displaying the signal detected by said signal detection means.

* * * * *

UNITED STATES PATENT AND TRADEMARK OFFICE
CERTIFICATE OF CORRECTION

| | | |
|---|---|---|
| PATENT NO. | : 7,267,750 B2 | Page 1 of 1 |
| APPLICATION NO. | : 10/466561 | |
| DATED | : September 11, 2007 | |
| INVENTOR(S) | : Motokazu Watanabe et al. | |

It is certified that error appears in the above-identified patent and that said Letters Patent is hereby corrected as shown below:

On the title page of the Letters Patent, item (56) References cited, FOREIGN PATENT DOCUMENTS, change "JP  7-110303  4/1995" to -- JP 7-110313 4/1995 --, and add -- JP 09-089831  4/1997 --

Signed and Sealed this

Twentieth Day of May, 2008

JON W. DUDAS
*Director of the United States Patent and Trademark Office*